United States Patent [19]

DeGraff, Jr.

[11] 4,407,958

[45] Oct. 4, 1983

[54] SLANT CULTURE TUBE RACK

[75] Inventor: Harold F. DeGraff, Jr., Rochester, N.Y.

[73] Assignee: Sybron Corporation, Rochester, N.Y.

[21] Appl. No.: 328,847

[22] Filed: Dec. 9, 1981

[51] Int. Cl.[3] .............................................. C12M 1/00

[52] U.S. Cl. .................................... 435/287; 422/104; D24/32

[58] Field of Search ................ D24/32; 422/102, 104; 435/287, 296, 299, 809

[56] References Cited

U.S. PATENT DOCUMENTS

D. 257,390 10/1980 Hahn et al. .......................... D24/32

4,060,457 11/1977 Iizuka et al. .................... 422/104 X 4,160,803 7/1979 Potts .............................. 422/104 X

OTHER PUBLICATIONS

Mallinckrodt, Science Products Division, Plastic Test Tube Rack Advertisement, Aug. 1982.

*Primary Examiner*—Ferris H. Lander

*Attorney, Agent, or Firm*—Robert A. Gerlach; Robert J. Bird; Roger Aceto

[57] ABSTRACT

Test tube rack for holding a plurality of test tubes in an upright position and further adapted for holding the test tubes at slant angles of 5° from horizontal and 20° from horizontal for the preparation and growth of agar slant tube cultures or liquid tube cultures. The racks are further adapted for positive interlock stacking.

3 Claims, 4 Drawing Figures

SLANT CULTURE TUBE RACK

BACKGROUND AND SUMMARY OF THE INVENTION

The subject matter of this invention is culture tube racks, and more particularly a culture tube rack to facilitate the preparation and growth of aerobic and anaerobic agar slant tube cultures, and liquid slant tube cultures.

Agar slant culture tubes are used in growing, storing, and testing of both aerobic and anaerobic organisms. The aerobic organisms are exposed on the surface and typically require a surface area of exposure to air. Conversely, the anaerobic organisms are disposed throughout the medium and should not have a surface exposure to air. The various desired distributions of culture media can be obtained by the angular positioning or tilt of the rack.

Agar medium is purchased in powder form for mixing with hot water. The medium is then placed in a culture tube and sterilized. While the medium is hot, it remains liquid. If a rack full of tubes is removed from a sterilizer and placed on its side, the medium will cool and solidify to a consistency of gelatin in a position slanted relative to the axis of the tube. This solidified sterile culture is then inoculated as desired with organisms.

Typically, agar slant culture tubes are prepared using standard tube racks by leaning them against some other object during cooling and solidifying. Such practice is necessarily inconvenient and furthermore the angle of the culture slant is estimated and therefore variable from one rack to the next.

This situation has been addressed in the prior art. One result is a rack having an angularly adjustible cradle. Another is a rack having a fixed 5° tilt angle with springs to hold the test tubes in place. Another is a rack having a protruding lip on which to rest the rack in an inclined position.

It is an object of the present invention to provide a culture tube rack which is adapted for holding culture tubes vertically, for holding them at a first angle from the horizontal as for aerobic cultures, for holding them at a second angle from the horizontal as for growing anaerobic cultures, and for convenient stacking of rack upon rack. It is also intended that the rack be used for holding and growing cultures, in the two slant positions, in a liquid medium.

The present invention is practiced in one form by a culture tube rack having end plates, with front edges extending upwardly and outwardly at 20° from the vertical, and rear edges extending upwardly and outwardly at 5° from the vertical, so that the rack can be positioned upright or at 5° or 20° slants for setting of media and growth of agar cultures. The end plates are furthermore configured for vertical nesting of one rack atop another.

DRAWING

DESCRIPTION

Figure 1:
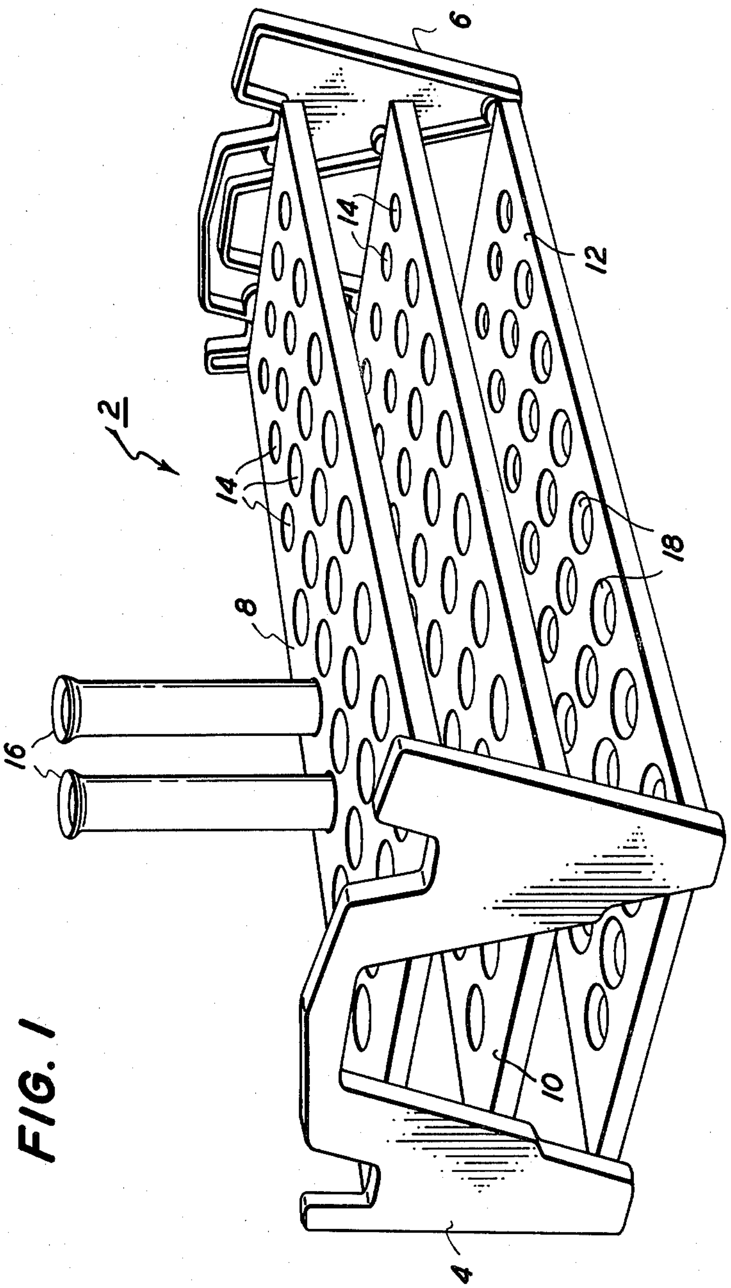
FIG. 1 is a perspective view of a culture tube rack according to this invention.

With reference to FIG. 1, the culture tube rack of the present invention is generally indicated at 2 and includes a left end plate 4 and a right end plate 6. A top and a bottom plate 12 are suitably mounted between the end plates 4 and 6. The top and middle plates 8, 10 are apertured as at 14 so that culture tubes 16 can be inserted through the apertures. The bottom plate 12 is apertured as shown at 18, the apertures being conical with the lower diameter culture smaller than the culture tube diameter to provide a bottom rest for the culture tubes.

Figure 2:
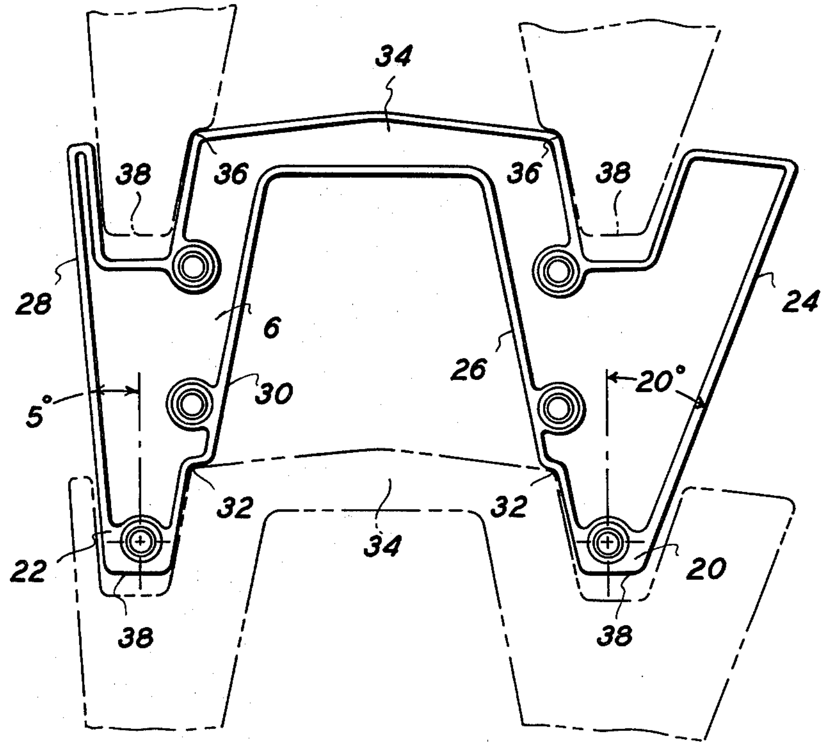
FIG. 2 is a view, as from the inside of the rack shown in FIG. 1, of the right end piece of the rack.

Referring now to FIG. 2, end plate 6 includes a front leg member 20 and a rear leg member 22. The front leg member 20 extends upwardly from its foot and outwardly at a 20° angle from the vertical to a height somewhat above the center of gravity of the tube rack. Similarly, the rear leg 22 extends upwardly from its foot and outwardly at a 5° angle from the vertical to a height above the center of gravity of the rack.

Front leg 20 includes a front edge 24 and an inside edge 26. Rear leg 22 includes a rear edge 28 and an inside edge 30. Inside edges 26 and 30 are configured to include shoulder abutments 32. The top central portion 34 of end plates 4 and 6 includes front and rear shoulders 36.

Figure 3:
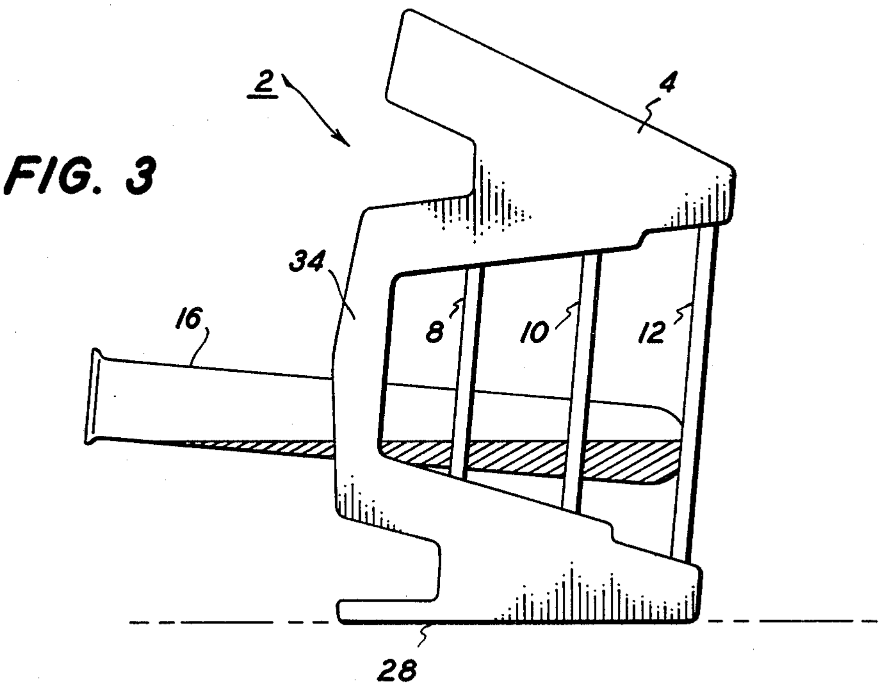
FIG. 3 is an end view of the rack shown lying on one of its sides.

Referring now to FIG. 3, the culture tube rack is shown resting on the rear edges 28 of the end plates, thus to incline the culture tubes upward at an angle of 5° from the horizontal. As illustrated, this provides a substantial surface area for the growth of aerobic organisms.

Figure 4:
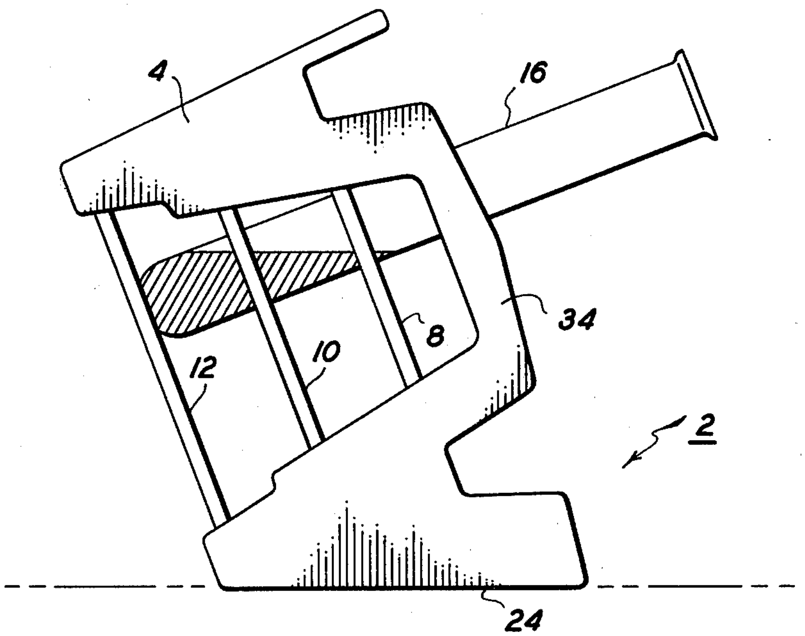
FIG. 4 is an end view of the rack shown lying on its other side.

Referring now to FIG. 4, the rack is shown resting on its front edges 24 so as to incline the culture tubes upward at an angle of 20° from the horizontal. This provides a greater depth of culture to facilitate implantation in the medium for the growth of anaerobic organisms. The relatively larger depth of medium provided by this 20° slant helps to prevent the medium from drying out in storage.

In both the 5° position of FIG. 3 and the 20° position of FIG. 4, the length of the respective edges 28 and 24 on which the rack is resting is sufficient to keep the rack from toppling over. In other words, the inclined edges extend beyond the center of gravity of the rack with the culture tubes mounted in it.

Referring back to FIG. 2, an additional feature of the tube rack of this invention is illustrated. The configuration of the end pieces 4, 6 permits stacking of one rack atop another. The shoulder abutments 32 on the inside edges 26, 30 of the end plates of one rack rest on the shoulders 36 of the rack beneath it. The lower foot portions 38 of the front and rear legs hang down into the cavities formed between the top central portion 34 and the upper extensions respectively of the front and rear legs 20, 22. Frontward or rearward sliding of one rack on another is thus prevented by this positive interlocking. Sidewise slippage is also prevented, by the positive abutment of the top central portion 34 of the lower rack with the bottom plate 12 of the rack nesting upon it.

With the combination of features described, the culture tube rack of this invention can be stacked for storage, then used for autoclaving, or with a 5° slant for aerobic organism growth, or with a 20° slant for anaerobic organism growth, all without changing racks, or otherwise improvised handling.

What is claimed is:

1. A culture tube rack for preparation and growth of cultures, including:

a plurality of apertured plates for holding culture tubes in a generally upright position, said plates being mounted between right and left upright end plates, said end plates each including a front and a rear leg member, said front leg member having a front edge extending upward and forward to a height above the center of gravity of said rack, said rear leg member having a rear edge extending upward and rearward to a height above the center of gravity of said rack, said end plates being so configured that the front and rear leg members of one of said end plates straddle the corresponding end plate of another such tube rack for positive interlock stacking of a plurality of said racks, whereby said rack is selectively positionable upright on said front and rear foot portions, or at a first angle of tube slant, or at a second angle of tube slant.

2. A culture tube rack as defined in claim 1 in which one of said leg members extends at a 5° angle from the vertical and the other of said leg members extends at a 20° angle from the vertical.

3. A culture tube rack for preparation and growth of cultures, including:

a plurality of parallel apertured plates for holding culture tubes in a generally upright position, said plates being mounted between upright end plates, said upright end plates having:

i. bottom portions on which to rest said rack in its upright position, ii. front and rear edges inclined from the vertical on which to rest said rack in respectively forward and rearward inclined positions, and iii. top portions to support the bottom portions of corresponding end plates of another such tube rack for positive interlock stacking of a plurality of such racks.

* * * * *